US011712202B2

(12) United States Patent
Lin

(10) Patent No.: US 11,712,202 B2
(45) Date of Patent: Aug. 1, 2023

(54) VEIN DETECTION DEVICE

(71) Applicant: Shih-Min Lin, Taichung (TW)

(72) Inventor: Shih-Min Lin, Taichung (TW)

( * ) Notice: Subject to any disclaimer, the term of this patent is extended or adjusted under 35 U.S.C. 154(b) by 1280 days.

(21) Appl. No.: 16/172,696

(22) Filed: Oct. 26, 2018

(65) Prior Publication Data

US 2019/0388023 A1 Dec. 26, 2019

(30) Foreign Application Priority Data

Jun. 22, 2018 (TW) ................... 107121617

(51) Int. Cl.
*A61B 5/00* (2006.01)
(52) U.S. Cl.
CPC ............ *A61B 5/489* (2013.01); *A61B 5/0059* (2013.01); *A61B 5/0082* (2013.01)
(58) Field of Classification Search
CPC ....... A61B 5/489; A61B 5/0059; A61M 5/427
See application file for complete search history.

(56) References Cited

U.S. PATENT DOCUMENTS

| 6,230,046 | B1 | 5/2001 | Crane et al. |
| 2004/0171923 | A1* | 9/2004 | Kalafut ................ A61B 5/0059 600/407 |
| 2008/0194930 | A1 | 8/2008 | Harris et al. |
| 2009/0318891 | A1 | 12/2009 | Marcotte et al. |
| 2015/0327765 | A1 | 11/2015 | Crane et al. |
| 2017/0188937 | A1* | 7/2017 | Ike ........................ A61B 5/6824 |
| 2018/0092698 | A1* | 4/2018 | Chopra .................. A61B 90/39 |

FOREIGN PATENT DOCUMENTS

| CN | 201006081 Y | 1/2008 | |
| CN | 202843582 U | 4/2013 | |
| CN | 104665766 A | 6/2015 | |
| CN | 204562100 U | 8/2015 | |
| CN | 105997013 A | * 10/2016 | ............. A61B 5/489 |
| CN | 206597199 U | 10/2017 | |
| CN | 107788949 A | 3/2018 | |
| DE | 202010000522 U1 | 8/2010 | |
| JP | H4-118516 U | 10/1992 | |
| JP | H7-140329 A | 6/1995 | |
| JP | H11-203452 A | 7/1999 | |
| JP | 2000-300568 A | 10/2000 | |
| JP | 2010-218 A | 1/2010 | |
| JP | 2015-507493 A | 3/2015 | |
| JP | 6047847 B1 | 12/2016 | |
| JP | 2018-79326 A | 5/2018 | |

(Continued)

OTHER PUBLICATIONS

Rob Knight, titled "Bracketing for HDR with Nikon DSLRs", Feb. 26, 2010, The Digital Photo Experience, 1 page (Year: 2010).*

*Primary Examiner* — James M Kish

(74) *Attorney, Agent, or Firm* — Cheng-Ju Chiang

(57) ABSTRACT

This invention discloses a vein detection device, comprising a base, a transmitter, a detection arm and at least one receiver. The emitter is an infrared emitter which comprises a fisheye lens. An exposure portion close to the fisheye lens of the transmitter is exposed by an infrared light, thus the infrared light transforms into an infrared image which is received by the at least one receiver. A vein image is displayed on a screen which is configured on the base.

8 Claims, 3 Drawing Sheets

(56) References Cited

FOREIGN PATENT DOCUMENTS

| | | | | |
|---|---|---|---|---|
| KR | 2010-0123021 | * | 11/2010 | ............. A61B 5/489 |
| KR | 10-2013-0102339 A | | 9/2013 | |
| KR | 10-2015-0044783 A | | 4/2015 | |
| TW | 254195 U | | 1/2005 | |
| TW | M384667 U1 | | 7/2010 | |
| TW | 201813582 A | | 4/2018 | |
| TW | 201813589 A | | 4/2018 | |
| WO | 96/36273 A2 | | 11/1996 | |
| WO | 2014/079875 A2 | | 5/2014 | |
| WO | 2014/079875 A3 | | 5/2014 | |
| WO | 2016/098449 A1 | | 6/2016 | |
| WO | 2017/115512 A1 | | 7/2017 | |
| WO | 2018/110807 A1 | | 6/2018 | |

\* cited by examiner

VEIN DETECTION DEVICE

TECHNICAL FIELD

The present invention relates to a vein detection device, particularly, to a vein detection device which can display vein images captured by infrared light sensing technology.

BACKGROUND OF RELATED ARTS

In traditional western medical system, there are hundreds of ways to give medicine cure. The common ways include oral drugs, injections, drip medicaments or suppositories.

However, the administration of injections has been an indispensable way of medical practice. Generally speaking, the most common way of injecting is by intravenous injection for giving medicine in safety. The reason for this is that venous blood pressure is lower and therefore less likely to produce a high risk of bleeding after invasive treatment.

However, the traditional intravenous injection relies on the experience of medical staff. Leaving aside the experience of the medical staff, there is an issue in clinic that many patients have difficulty in finding blood vessels. The reason may be that the innate blood vessels are thinner, or the adipose tissue thickness is too high, and the blood vessels are not easily detected by the naked eye from the outside of the skin. Although veins can also be shown by girdling, it is still very limited.

For the above-mentioned reasons, modern venous sensing devices have been developed in modern medicine. Traditional venous sensing devices are based on the principle that absorptivity for near-infrared light of hemoglobin in blood vessels is different from that of other tissues. The position of the subcutaneous blood vessels is projected onto the skin surface through image processing after near-infrared light imaging. The medical personnel can clearly identify the distribution of blood vessels under the skin of patients.

More specifically, for traditional vein sensing devices, when near-infrared light irradiates a site of a human body, a specific wavelength of infrared light is absorbed by the blood vessels. The more it absorbs, the less it reflects, so the image projected onto the skin looks black. The less the other tissues absorb, the more they reflect, so that they will show higher brightness color.

However, the traditional venous sensing devices eventually display vascular images on the skin surface by projecting visible light. Therefore, the projected vascular images are easily deviated from the actual location of the vein. In this way, a needle will not penetrate into the right place of injection.

SUMMARY

To resolve the drawbacks of the prior arts, the present invention discloses a vein detection device, comprising a base, a transmitter, a detection arm, a first receiver and a display.

The transmitter is configured on the base, wherein the transmitter is attached to an exposed portion to emit an infrared light to the exposed portion. The detection arm is configured on the base, and it is used to support the first receiver. The first receiver receives a first infrared light image coming from the exposed portion, and the first infrared light image is converted from the infrared light.

A display is configured on the base and electrically connected with the first receiver to display a first vein image converted from the first infrared light image. The transmitter includes a lens which may be attached by the exposed portion.

Embodiments of the invention are illustrated by way of example, and not by way of limitation, in the figures of the accompanying drawings in which like reference numerals refer to similar elements.

DETAILED DESCRIPTION OF THE INVENTION

In order to understand the technical features and practical efficacy of the present invention and to implement it in accordance with the contents of the specification, hereinafter, preferred embodiments of the present invention will be described in detail with reference to the accompanying drawings.

Figure 1:
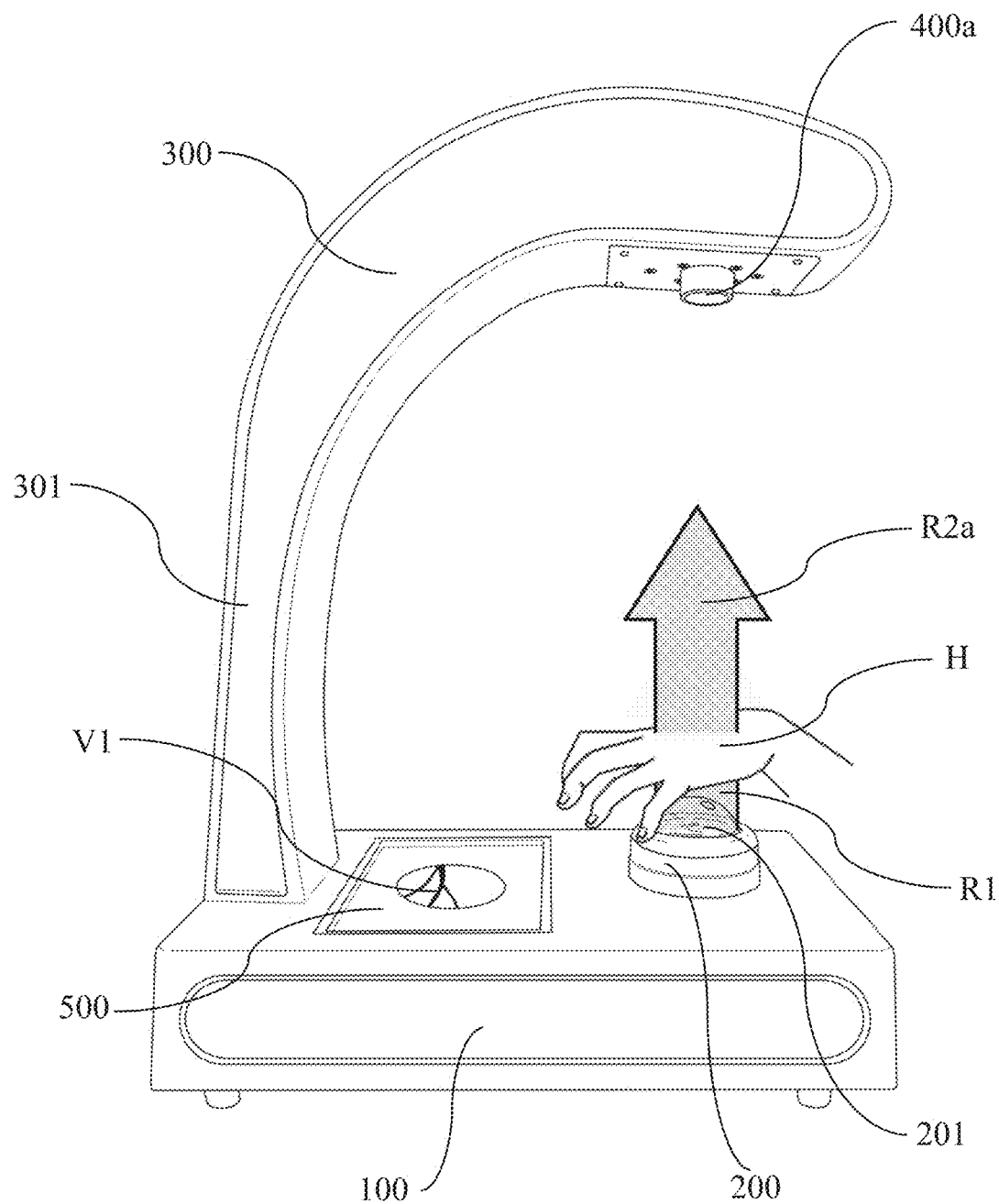
FIG. 1 is a schematic diagram of the appearance structure of an embodiment of the present invention.

Referring to FIG. 1, it shows a schematic diagram of the appearance structure in accordance with one embodiment of the present invention. As shown in FIG. 1, the configuration of the vein detection device 10*a* of the present invention is illustrated in the embodiment of FIG. 1, mainly including a base 100, a transmitter 200, a detection arm 300, a first receiver 400*a*, and a display 500.

The transmitter 200 is configured (mounted) on the base 100. The transmitter 200 of this embodiment is an infrared light transmitter. The transmitter 200 is closely attached to the exposed portion H and emits infrared light R1 to irradiate the exposed portion H. In this embodiment, an infrared light R1 has wavelengths ranging from 780 to 1400 nanometers (nm), and the exposed portion H is a palm of the human hand. In addition, the exposed portion H can also be a common intravenous injection site including but not limited to thigh, buttock, upper arm, etc.

The detection arm 300 of the embodiment is configured on the base 100, and the detection arm 300 is used to support (mount) the first receiver 400*a*. In this embodiment, the detection arm 300 may be provided with at least one joint portion 301 to adjust the position of the first receiver 400*a*. In addition, the first receiver 400*a* of the present embodiment is an infrared camera, and the first receiver 400*a* receives a first infrared image R2*a* coming from the exposed portion H. Actually, the first infrared image R2*a* is the image converted from the infrared light R1 passing through the exposed portion H. The first infrared image R2*a* contains the image information of various tissues irradiated by the infrared light R1.

In this embodiment, the first infrared image R2*a* actually includes a first brightness interval image, a vein brightness interval image and a second brightness interval image. The brightness of the first brightness interval image is higher than the brightness of the vein brightness interval image, and the brightness of the vein brightness interval image is higher than the brightness of the second brightness interval image.

As an example of the tissue that may be contained in the actual exposed portion H, the infrared light R1 is almost absorbed by the vein, so only the image of a certain depth (brightness) interval is taken as the vein brightness interval image. However, the first brightness interval image and the second brightness interval image defined by the brightness respective higher and lower than that of the vein brightness interval image may include but not limited to bone tissue image, connective tissue image, adipose tissue image, cartilage tissue image or other tissue cells image.

Therefore, the display 500 of this embodiment is arranged on the base 100 and electrically connected with the first receiver 400a. And, the display 500 displays a first vein image V1 converted from the first infrared image R2a. Furthermore, the first vein image V1 is a conversion image of the above vein brightness interval image, and the first vein image V1 can clearly show the location of the vein.

In this embodiment, the transmitter 200 contains a lens 201. The lens 201 is closely attached to the exposed portion H. In the present invention, the term "closely" does not refer to proximity, but also include actual physical contact, which belong to the definition category of the present invention.

In this embodiment, the lens 201 is a fisheye lens, and further, it can be a fisheye lens module. The lens 201 is used to control emitting direction of infrared light R1 emitted by the transmitter emit 200. The emitting direction of the infrared light R1 is adjusted based-on the position of the exposed portion H and the first receiver 400a. Therefore, through the above-mentioned technical means, it can easily achieve the requirement in this embodiment that the first receiver 400a, the irradiated unit H and the transmitter 200 are located on the same straight line.

In other words, the transmitter 200 essentially contains a function of omnidirectionally tracking the location of the exposed portion H. Therefore, the position of the first receiver 400a must also be adjusted through other means, such as at least one joint portion 301, to conform to the definition of the same straight line.

Figure 2:
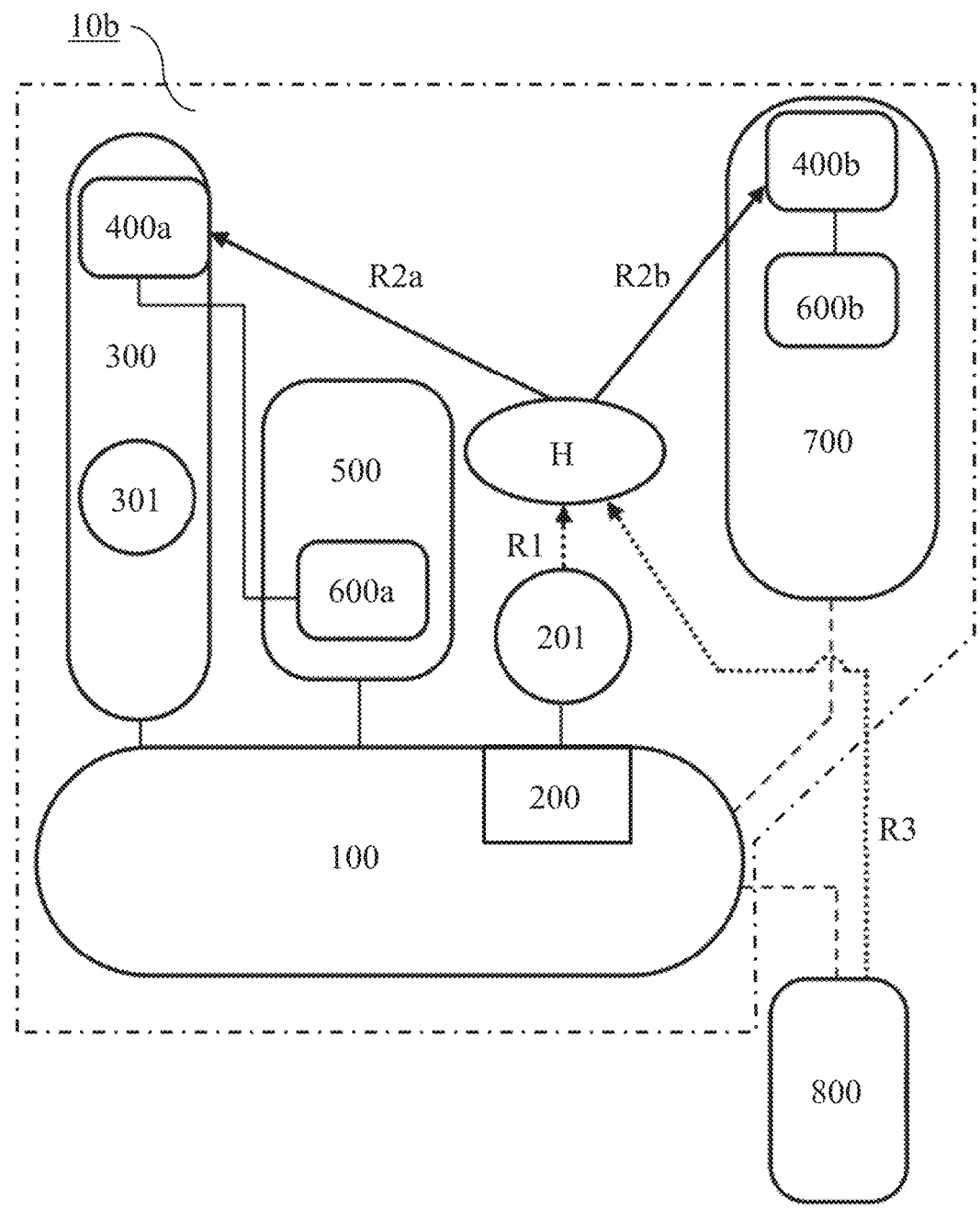
FIG. 2 is a system architecture diagram in accordance with one embodiment of the present invention.
Figure 3:
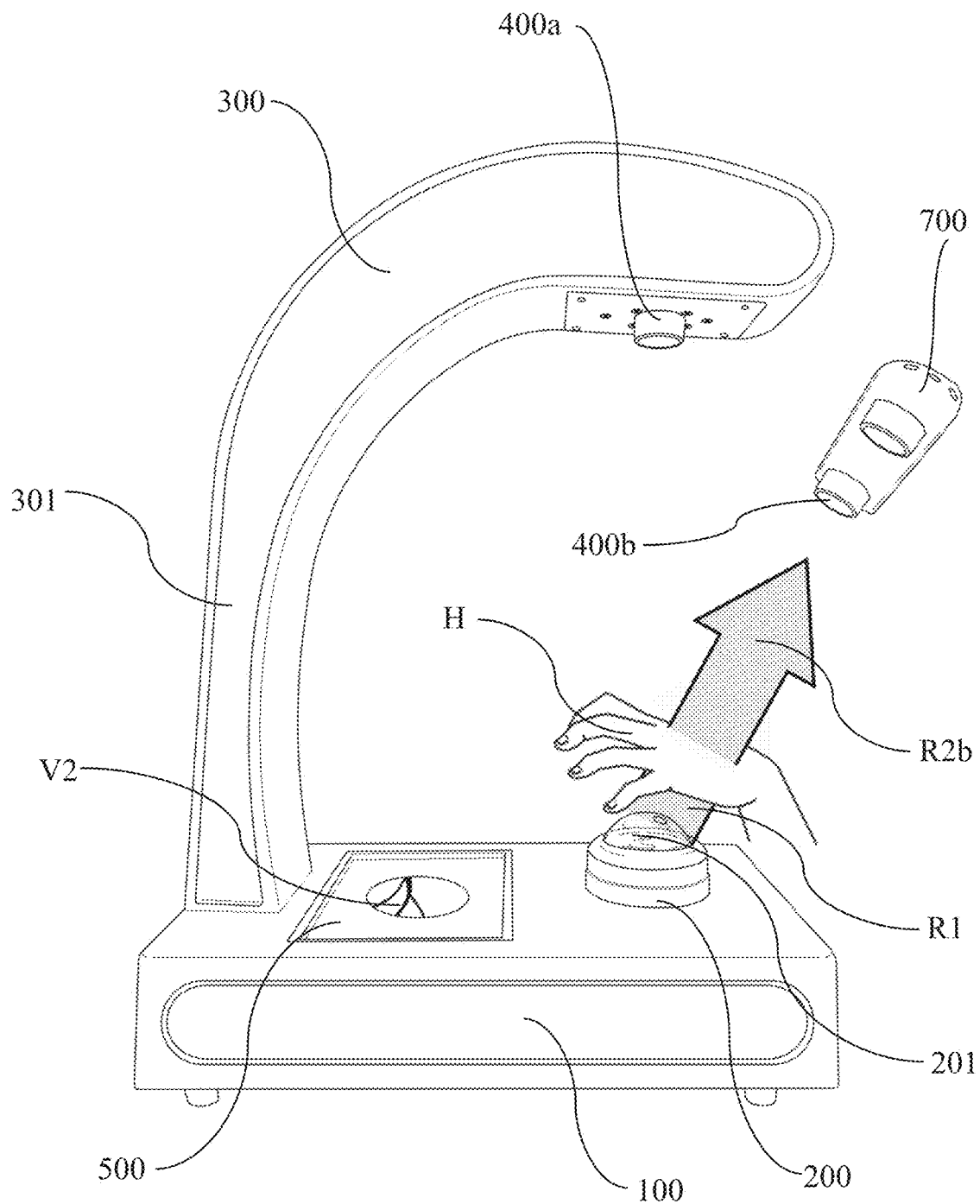
FIG. 3 is a schematic diagram of the appearance structure of another embodiment of the present invention.

Referring to FIG. 2 and FIG. 3, FIG. 2 is a system architecture diagram of another embodiment of the present invention, and FIG. 3 is an appearance structure diagram of further embodiment of the present invention. Compared with the embodiment of FIG. 1, the system architecture of the embodiment in FIG. 2 further includes a head-mounted display 700 and an auxiliary transmitter 800, while the embodiment in FIG. 3 further includes a head-mounted display 700.

To enable the implementation of FIGS. 1-3 of the present invention, it should be noted that a power supply, a memory, a wireless signal transceiver module and microcontroller may be provided within the base 100 to provide the power required for the operation of the vein detection device 10a and the vein detection device 10b, as well as the ability to calculate and process images. In practice, the above-mentioned components can be configured as required, and the detailed descriptions are omitted in this embodiment.

In the embodiments of FIG. 2 and FIG. 3, the base 100 of the vein detection device 10b may be wired or wirelessly electrically connected to the head-mounted display 700. Further, the head-mounted display 700 may include but not limited to a virtual reality (VR) display or an augmented reality (AR) display. Therefore, the person skilled in the art should realize that the head-mounted display 700 may also include components required for operation, such as a wireless signal transceiver module, a power supply device, a microcontroller, a memory and a display card, which detailed descriptions are omitted.

In the embodiment of FIG. 2 or FIG. 3, the head-mounted display 700 is further provided with a second receiver 400b, and a second infrared image R2b coming from the exposed portion H is received by the second receiver 400b, so that the second infrared image R2b is converted to a second vein image V2 and then displayed on the display 500 and the head-mounted display 700 (The display screen is located inside the head-mounted display 700, so FIG. 3 does not indicate the location of the second vein image V2). In other words, in the embodiment of FIG. 3, the second vein image V2 can also be synchronously displayed on the display 500 of base 100. Thus, the second vein image V2 captured by the head mounted display 700 can be seen by other people.

Based-on the indication of FIG. 2, it can be seen that in the embodiments of FIG. 1 and FIG. 3, the display 500 is provided with a first image filtering module 600a and the head-mounted display 700 is provided with a second image filtering module 600b, and the first image filtering module 600a and the second image filtering module 600b are connected with the first receiver 400a and the second receiver 400b, respectively. When the first infrared image R2a is transmitted to the first receiver 400a or the second infrared image R2b is transmitted to the second receiver 400b, the first image filtering module 600a and the second image filtering module 600b are filtered out the first brightness interval image and the second brightness interval image, and only the vein brightness interval image is retained so that the vein brightness interval image is formed to be the first venous image V1 or the second venous image V2 and then displayed on the display 500 of the base 100 or the head-mounted display 700.

Therefore, the image filtering module 600a, 600b in this embodiment can include but not limited to the combination of a filter and a digital signal processor.

As can be seen from the diagram of FIG. 3, the transmitter 200, the exposed portion H and the second receiver 400b are arranged on a straight line to perform a good detection process. In the embodiment of FIG. 2, the position of the second receiver 400b can be easily adjusted as the head-mounted display 700 moves. Similarly, in the absence of a head-mounted display 700 in the embodiment of FIG. 1, if the exposed portion H or the transmitter 200 cannot be located on the same straight line with the first receiver 400a, the detection arm 300 in the embodiment of FIGS. 1-3 may be provided with at least one joint portion 301 (such as embedded into the detection arm 300) such that the angle and position of the first receiver 400a can be adjusted arbitrarily by an operator. At least one of the above-mentioned joint portion 301 may be any kind of mechanical joint structure, including not limited to an axial joint, a spherical joint, an omnidirectional joint, and the combination thereof.

In the embodiment of FIG. 2, the vein detection device 10b may be connected to an auxiliary transmitter 800. For example, the auxiliary transmitter 800 can be wired or wirelessly connected to the base 100 of the vein detection device 10b. In this embodiment, the auxiliary transmitter 800 is also an infrared transmitter to emit an auxiliary infrared light R3 to irradiate the exposed portion H. The purpose of using the auxiliary transmitter 800 is that when the first infrared image R2a or the second infrared image R2b is unable to be observed by the vein detection device 10b, the auxiliary transmitter 800 can provide the auxiliary infrared light R3 from another dimension (position) to the exposed portion H. Thus, by multi-directional light source imaging, the first infrared image R2a sensed by the first receiver 400a or the second infrared image R2b sensed by the second receiver 400b can be seen clearly.

In other possible implementation scenarios, the detection arm 300 can include a built-in wireless communication transceiver module. As the detection arm 300 is removed from the base 100, it is still capable of communicating with the base 100 and the first receiver 400*a* is allowed to detect the first infrared image R2*a* coming from the exposed portion H in a free direction.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed is:

1. A vein detection device, comprising:
   a base;
   a transmitter configured on said base, wherein said transmitter emits an infrared light to said exposed portion;
   a detection arm configured on said base;
   a first receiver configured on said detection arm to receive a first infrared light image coming from said exposed portion, wherein said first infrared light image is converted from said infrared light; and
   a display configured on said base and electrically connected with said first receiver to display a first vein image converted from said first infrared light image;
   wherein said transmitter includes a lens;
   wherein said display is provided with a first image filtering module to connect with said first receiver;
   wherein said first image filtering module includes combination of a filter and a digital signal processor;
   wherein said lens is a fisheye lens;
   wherein said detection arm comprises a built-in wireless communication transceiver module;
   wherein said detection arm is detachably removed from the base;
   wherein said detection arm communicates with the base and the first receiver, allowing the first receiver to detect the first infrared light image coming from said exposed portion in a free direction.

2. The vein detection device of claim 1, wherein said base is wired or wireless connected with a head-mounted display, wherein said head-mounted display is provided with a second receiver to receive a second infrared light image coming from said exposed portion such that said second infrared light image is converted as a second vein image to display on said head-mounted display;
   wherein said second infrared light image includes a first brightness interval image, a vein brightness interval image and a second brightness interval image, wherein a brightness of said first brightness interval image is higher than that of said vein brightness interval image, and a brightness of said vein brightness interval image is higher than that of said second brightness interval image, wherein said head-mounted display includes a second image filtering module connected to said second receiver to filter out said first brightness interval image and said second brightness interval image such that said vein brightness interval image is formed to be said second vein image;
   wherein said second image filtering module includes combination of said filter and said digital signal processor.

3. The vein detection device of claim 2, wherein said first receiver or said second receiver is an infrared camera.

4. The vein detection device of claim 2, wherein one of said first receiver and said second receiver is arranged on a straight line with said exposed portion and said transmitter.

5. The vein detection device of claim 1, wherein said first infrared light image includes a first brightness interval image, a vein brightness interval image and a second brightness interval image, wherein a brightness of said first brightness interval image is higher than that of said vein brightness interval image, and a brightness of said vein brightness interval image is higher than that of said second brightness interval image.

6. The vein detection device of claim 5, wherein said first image filtering module is filtered out said first brightness interval image and said second brightness interval image such that said vein brightness interval image is formed to be said first vein image.

7. The vein detection device of claim 1, further comprising an auxiliary transmitter connected to said base to emit an auxiliary infrared light to irradiate said exposed portion.

8. The vein detection device of claim 1, wherein said detection arm includes a joint portion.

* * * * *